United States Patent [19]

Tornberg

[11] Patent Number: 4,856,335
[45] Date of Patent: Aug. 15, 1989

[54] METHOD OF ESTABLISHING STANDARD COMPOSITE MATERIAL PROPERTIES

[75] Inventor: Neal E. Tornberg, San Diego, Calif.

[73] Assignee: The Expert System Technologies, Inc., San Diego, Calif.

[21] Appl. No.: 111,694

[22] Filed: Oct. 21, 1987

[51] Int. Cl.⁴ ............................................. G01N 29/00
[52] U.S. Cl. ........................................ 73/597; 73/818
[58] Field of Search ................ 73/597, 599, 818, 820, 73/821, 822, 825, 866, 32 A

[56] References Cited

U.S. PATENT DOCUMENTS

| 3,504,532 | 4/1970 | Muenow et al. | 73/597 |
| 3,715,709 | 2/1973 | Zacharias, Jr. et al. | 73/597 |
| 3,786,676 | 1/1974 | Korolyshun et al. | 73/818 |
| 3,995,501 | 12/1976 | Wiley | 73/597 |
| 4,616,508 | 10/1986 | Jorn | 73/825 |
| 4,754,645 | 7/1988 | Piche et al. | 73/597 |

FOREIGN PATENT DOCUMENTS

0659933  4/1979  U.S.S.R. ............................. 73/821

Primary Examiner—Stewart J. Levy
Assistant Examiner—Robert R. Raevis
Attorney, Agent, or Firm—Gregory O. Garmong

[57] ABSTRACT

A standard reference deformation of a composite material containing a flowable phase and compressible inclusions, such as a prepreg, is measured as the deformation whereat the dominant compressive mode of composite deformation changes from that characteristic of compressible inclusion collapse to that characteristic of resin flow, termed the optimal consolidation deformation. Establishment of this point permits measurement and correlation of physically significant composite properties. For example, material properties of such composite materials are measured under a compressive loading by an ultrasonic transducer at the optimal consolidation deformation. At this point, normally determined to be the deformation at which the second derivative of compressive displacement falls to about zero, compressible inclusions such as voids are eliminated but the flowable phase has not yet begun to flow significantly so as to change the fractions of the phases. This technique is particularly valuable in ultrasonically measuring properties such as phase fractions of resin matrix prepreg materials wherein the resin has not been cured and readily flows, and wherein there are typically voids that interfere with the measurement of properties.

18 Claims, 5 Drawing Sheets

METHOD OF ESTABLISHING STANDARD COMPOSITE MATERIAL PROPERTIES

BACKGROUND OF THE INVENTION

This invention relates to the accurate and precise characterization and measurement of deformation and properties of composite materials, and, more particularly, to the measurement of the properties of composites containing compressible inclusions such as voids.

Composite materials are important structural materials used in aerospace and other applications. A composite material contains two or more separate phases which retain their distinct properties within the composite. In a typical non-metallic aerospace composite material, high strength or high modulus reinforcements such as graphite, glass or Kevlar fibers are embedded in a matrix of a resin material that is much weaker and more ductile than the reinforcement. The matrix bonds together, aligns, and protects the reinforcement.

One of the most significant aspects of composite materials is that designers can tailor the properties of the material to the requirements of each individual piece of structure, so as to minimize weight and maximize performance. The composite properties are determined by the individual properties of the reinforcement and the matrix phases, and by the relative amounts of the reinforcement and the matrix present in the composite material. The properties of each batch of composite material must be known to be certain that they meet the requirements of the designer for a particular application. Since the properties of the phases of the composite remain relatively constant, it is vital that the amounts, or fractions, of the phases be known accurately for each piece of the composite material.

Although based upon sound engineering principles, today's technology of fabricating high performance structural composite laminate is not yielding the part-to-part reliability that will be required of the larger, more complex structures currently on the drawing boards. Some of the major problems in achieving this reliability are the occurrence of voids, and the lack of adequate nondestructive methods to monitor composite properties. To understand the difficulties in determining that composite properties meet design tolerances as well as in monitoring the occurrence of voids during the manufacturing process, it is necessary to understand the manner in which composite materials are manufactured.

In the manufacturing of a typical polymer-matrix composite, the fibers, usually in the form of yarns or bundles, are impregnated with the matrix resin to form a precursor material, called "prepreg". The fibers are hard and strong, while the resin is soft and flowable under pressure. Individual sheets or plies of prepreg are available in thicknesses of about 0.004–0.008 inches, with a layer of a release paper on each side of the sheet to facilitate handling. Due to air entrapment during the impregnation process, the prepreg sheets usually contain several percent voids therein, and also may have irregular surfaces.

Structures are progressively formed by stacking together or "laying up" a number of sheets of prepreg (after the release paper has been removed), which can result in further trapped air and voids due to the irregular surfaces of the sheets. The prepreg is slightly tacky to the touch, so that the lay-up is lightly bonded together and retains its shape. The lay-up is then cured by placing it into a press or an autoclave under elevated temperature and pressure. The curing induces a chemical reaction in the resin matrix material which causes it to become stronger, and also causes the adjacent sheets of prepreg to bond together. Void removal during the manufacturing process is essential to ensure structural strength and integrity of the finished parts. The desired result is a well-bonded, void-free structural part which has been tailored to have specific properties through careful selection of the constituent phases, the volume fractions, the manner in which the sheets are laid up, the curing process, and the state of cure-advancement in the starting prepreg material. Such parts are finding use in high performance aircraft, commercial aircraft, and a variety of more common applications.

In manufacturing practice it is extremely difficult to establish that voids have been removed, that the composite properties of the part meet design specifications, and that the prepreg is properly staged before curing. For example, determining the amount, or fraction, of the phases actually present in a specimen of prepreg composite material is difficult. The presence of voids further confuses the determination of phase fractions, since it is difficult to distinguish between the presence of voids and a higher fraction of a low density phase, by measurements of the externally measurable properties of the material. The same problem exists for the measurement of other properties such as viscosity which indicate state of advancement of prepreg material and the establishment of processing procedures for the composite material made from the prepreg. Manufacturers typically sell the prepreg material to volume fraction specifications, including a target volume fraction and a limit of variation, such as $+/-2$ percent. The users have to rely upon these figures in designing the layup and curing process, as well as to assume that the prepreg has not advanced in state of cure after its manufacture, since there is no adequate means to check these properties of the uncured prepreg.

The fabrication of prepreg to exact specifications is challenging, since the resin is flowable to permit the reinforcement to be embedded therein. The fibers are often provided in bundles or tows, which are dispersed within the resin in an ordered manner. Even though great care is taken to achieve uniformity of phase fraction and distribution, there are sometimes deviations from the specified target and from the required limits of variation.

It would be desirable for both the manufacturer and the user to be able to quickly and accurately determine the fractions of the reinforcement and matrix phases, and the amount of compressible inclusions such as voids, in the prepreg. In the past, the conventional approach for determining fractions of the phases has been by a laborious and costly destructive measurement technique. A piece of the prepreg is cut away from the rest of the material and weighed. The resin matrix is then chemically removed, leaving only the reinforcement particles. The particles are weighed, and the weight is divided by the total weight of the piece to determine weight fractions of the phases, from which volume fractions can be derived if desired. The fraction of matrix is calculated as one minus the fraction of the reinforcement.

This existing test procedure typically costs from $20 to $30 per specimen and requires 20–30 minutes to perform, with the result that relatively few specimens are tested. Because of the destructive nature and lengthy time requirements of the existing procedures, the test results cannot be used for real-time control of the manufacturing operation. As a result, entire batches of off-specification prepreg may be prepared before test results are available to know of the deviation from specification.

Accordingly, there exists a need for an approach for understanding, characterizing, and measuring the behavior of void-containing composites having a flowable matrix. In relation to the problem of most immediate interest, determination of phase fractions, such an approach would permit determination of the fractions of the phases and voids in composite materials by nondestructive measurements. Such a need is particularly acute for prepreg sheets, where a substantial fraction of internal voids is present. The present invention fulfills this need, and further provides related advantages.

SUMMARY OF THE INVENTION

The present invention provides a systematic process for accurately and precisely measuring that set of conditions in uncured composite materials, here termed "optimal consolidation", which leads to a repeatable physical state for purposes of reliable testing and processing. The method permits the determination of readily correlated physical properties to be made in about one minute and at a cost of only a few dollars per specimen tested. The content of compressible inclusions such as voids is indicated, and the effects of the presence of these inclusions are accounted for by the process, so that the effective properties of the composite material are determined. Large amounts of composite material may be determined and the results used to actively adjust manufacturing parameters. The process is particularly useful for determining the effective fractions of the phases present in prepreg as it is being manufactured, or thereafter, without destroying the prepreg itself. Tests can be performed nondestructively throughout sheets of the material, without cutting out samples for destructive testing.

In accordance with the invention, a process for measuring a standard reference deformation for a composite material comprises the steps of furnishing a specimen of a multiphase material wherein at least one phase is flowable, and which initially contains compressible inclusions within the specimen; compressing the specimen; and determining the deformation at which the dominant compressive displacement behavior of the composite changes from that characteristic of compressible inclusion collapse to that characteristic of flow of the flowable phase, this deformation being the standard reference deformation.

More particularly, and in relation to the measurement of properties of the composite, a process for measuring a standard property of the phases of a multiphase material comprises the steps of furnishing a specimen of a multiphase material wherein at least one phase is flowable, and which initially contains compressible inclusions within the specimen; applying a compressive force to the specimen so that its deformation increases with increasing time; and measuring a property of the specimen at a standard specimen deformation at which the dominant compressive displacement behavior of the composite changes from that characteristic of compressible inclusion collapse to that characteristic of flow of the flowable phase, the property measured at this point being the standard value of the property for the multiphase material.

In a preferred embodiment of the invention, the specimen is locally compressed by a transducer which then is used to measure the property, as by an ultrasonic measurement. In accordance with this aspect of the invention, a process for determining a standard property of a composite material comprises the steps of furnishing a specimen of a multiphase material wherein at least one phase is flowable, and which initially contains compressible inclusions within the specimen; contacting at least one surface of the specimen with an ultrasonic transducer under a compressive pressure so as to compress the composite material; and measuring the ultrasonic property of the specimen at the deformation at which the dominant compressive displacement behavior of the composite changes from that characteristic of compressible inclusion collapse to that characteristic of flow of the flowable phase, the property measured at this point being the standard value of the property for the composite material.

Most specifically, the fractions of the phases of the composite material may be measured nondestructively by this approach, using ultrasonic wave propagation techniques. In accordance with this aspect of the invention, a process for measuring the fractions of the phases of a composite material comprises furnishing a specimen of a composite material having a reinforcement phase embedded within a flowable matrix phase, and further having voids therein; contacting at least one surface of the specimen with an ultrasonic transducer under a downward compressive pressure; determining the displacement of the transducer with time; measuring the velocity of ultrasonic wave propagation of the specimen as the dominant compressive displacement behavior of the specimen changes from that characteristic of void collapse to that characteristic of flow of the flowable phase; and calculating the fractions of the phases present in the composite material from the velocity of ultrasonic wave propagation measured in the step of measuring.

Composite materials such as prepreg typically contain a hard, elastic phase such as the fiber reinforcement, a soft flowable phase such as the uncured or partially cured resin matrix, and compressible inclusions such as voids or possibly other very weak phases. The compressible inclusions are ordinarily removed or collapsed during subsequent curing of the prepreg, but are present in the as-manufactured prepreg. Their presence complicates the understanding and measurement of composite and phase properties. It is an important feature of the present process that their influence is nullified so that the properties and behavior of the composite are directly measurable in a standard form that can be correlated with other measurements and observations.

The present invention is based upon careful observation of the mechanisms of compressive flow of the materials, and then the applicaiton of those observations to the problems of measurement and control of processes. It has been observed that the compressive deformation of the composite can be understood has having two components. The first component is a rapid collapse and closure of the compressible inclusions, and specifically the voids. The second component is the flow of the flowable phase, and specifically the flow and extrusion of the matrix. It has been further observed that, in the earliest portion of the compressive deformation, the collapse of the compressible inclusions is the most rapid or dominant mechanism of deformation. In the next portion of the compressive deformation, collapse and closure of the compressible inclusions is substantially complete, and the dominant mechanism of deformation is flow of the matrix. It should be understood that both mechanisms occur simultaneously, and that one or the other is the most rapidly occurring, or dominant mechanism during the stages indicated.

The transition point or level of deformation between deformation regimes in which void (or other compressible inclusion) collapse dominates and matrix flow dominates marks the consolidation of the voids (or other compressible inclusions) out of the specimen. This deformation level, termed the "optimal consolidation" point, is physically significant for the measurement of properties and for determining further consolidation of the composite in subsequent lay-up and pressure curing. The on-line measurement of properties of the composite, as in the preferred approach using ultrasonic techniques to determine phase fractions, is of immediate interest.

In the presently preferred approach, the ultrasonic transducer is pressed against the surface of the specimen of prepreg with a compressive force. This compressive force causes the specimen to deform, and the amount of linear, through-thickness deformation with time is readily measured as the displacement of the transducer. The rate of deformation is observed to be rapid initially, and then slow to a secondary low, generally continuous rate of deformation over a period of time. The initial rate of deformation has been attributed to the compression and closure of the voids in the specimen, as the voids are even more compliant and deformable than the resin. The secondary, slower period of deformation is a result of the deformation and extrusion of the flowable matrix material out of the region under the transducer.

The measurement of composite properties is made at the point of transition from the initial rapid deformation of the composite to the secondary slower deformation. Measurements taken during the initial rapid deformation period are inaccurate due to the presence of the voids, which are closed and removed during this period. Measurements taken during the secondary period of deformation are inaccurate because the flowable resin preferentially flows out of the volume under the transducer. Accurate measurements are obtained only at about the point of the transition between the two regimes, the optimal consolidation point, when the deformation changes from that characteristic of void compression to that characteristic of matrix flow.

The point of transition can be measured and determined in real time to be the point at which the second derivative of compressive displacement with time falls to about zero. The second derivative is initially observed to be very large, as the compressive displacement is predominantly accommodated by the compliant compression and closure of the voids. After the voids have closed, the displacement becomes approximately linear in time during resin extrusion, so that the second derivative is about zero. (The use of the term "about zero" has physical significance in this instance. To a good approximation, the deformation at small strains in the resin deformation region is linear with time, but in reality probably is exponential or otherwise nonlinear. The second derivative is therefore probably not exactly zero, but is nearly so. Moreover, the numerical technique for measuring the second derivative may cause some noise. Thus, the term "about zero" is taken to mean the deformation at which the second derivative is extrapolated to zero numerically or graphically.) Completion of the void closure stage, the point at which the second derivative falls to about zero, is the physically significant strain or deformation for the determination of phase fractions. The displacement from the beginning of compressive deformation to this point is an indication of the fraction of voids initially present, which in itself is useful in characterizing the composite.

In practice, the preferred approach is to make a continuous series of ultrasonic measurements as the transducer translates under the compressive load. The time required for each measurement is small, so that the transducer can be taken to be stationary during the measurement, to a good approximation. The transducer position is recorded as each transducer time or frequency measurement is taken, so that the distance of flight of the ultrasonic signal can be determined, if necessary. The transducer position is also analyzed as a function of time, apart from its use in conjunction with the ultrasonic measurement, to determine when the second derivative of the displacement with time falls to about zero. Once this point is reached, the ultrasonic measurement value corresponding to the near-zero second derivative is selected as the standard value. Further testing is then no longer necessary, and the compressive load is removed. Further testing could, of course, be continued to ascertain highly useful information related to properties such as the viscosity of the composite during matrix flow. However, such continued testing becomes increasingly destructive as the arrangement of fibers and matrix changes, and is not normally done in a production setting where the objective of the test is the nondestructive determination of phase fractions.

From a practical standpoint, and as will be discussed in greater detail subsequently, the approach of the invention permits the correlation of test data for composites with standards to calculate fractions of the phases with a high degree of accuracy and precision. Standards of known phase fractions somewhat close to those of the "unknown" specimens are prepared and used to calibrate the system. The specimens whose phase fractions are to be determined can be then measured and the phase fractions calculated using the calibration information to a high degree of reproducibility, with the result available within a minute or less.

It will be appreciated that the present invention provides an important advance in the art of evaluation of composite materials. Ultrasonic measurements can be made in a reproducible fashion at a constant point of correlation, in a rapid, accurate, and precise manner. Other features and advantages of the invention will be apparent from the following more detailed description of the preferred embodiment, taken in conjunction with the accompanying drawings, which illustrate, by way of example, the principles of the invention.

DETAILED DESCRIPTION OF THE PREFERRED EMBODIMENT

Figure 1:
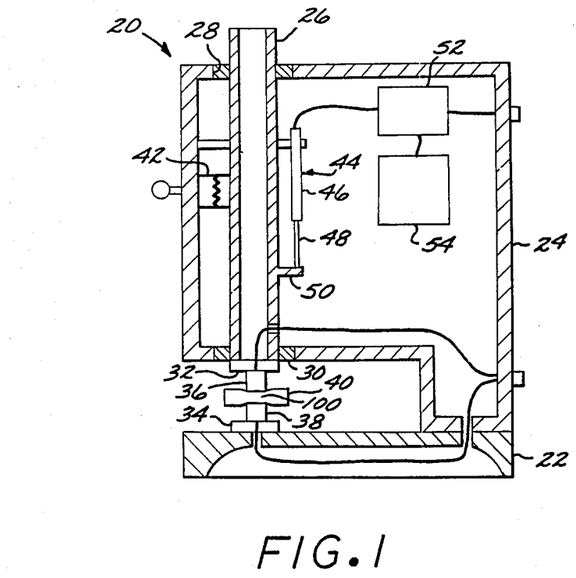
FIG. 1 is an apparatus used to perform measurements of specimens.

The present invention is used in conjunction with an apparatus 20, illustrated in FIG. 1 for applying a loading to a specimen. The apparatus 20 includes a rigid base 22 and an upright housing 24 set thereupon. The base 22 and housing 24 are formed of a aluminum frame construction that is rigid yet provides internal space for the mounting of the remainder of the apparatus 20.

A sliding rod 26 is mounted vertically yet slidably through bores 28 in the housing 24. Preferably, bearings 30 support the rod 26 within the bores 28. The rod 26 must be free to slide a sufficient distance to accommodate specimens of various sizes. The rod 26 may be hollow, as depicted, so that weights in the form of shot can be loaded therein to increase the dead-loading weight of the rod 26. Alternatively, weights can be added to the top end of the rod 26 to increase its weight, or an active loading mechanism, to be subsequently described, can be used.

A faceplate 32 is mounted at the lower end of the rod 26, in facing relation to a faceplate 34 mounted on the base 22. Ultrasonic transducers 36 and 38 are supported on the faceplates 32 and 34, respectively, in facing relation to each other. A specimen 40 under study is held between the transducers 36 and 38. The transducers 36 and 38 are preferably Etalon 5 MHz ultrasonic transducers. In operation, ultrasonic signals emitted by one of the transducers pass through the specimen 40 and are received by the other transducer, while the specimen 40 is locally compressed by the downward force exerted by the rod 26. The rod 26 can be raised by a hand operated gear mechanism 42 to remove the weight from the specimen 40, or lowered so that the transducers 36 and 38 press against the opposite faces of the specimen 40.

The precise vertical position of the rod 26 is measured by a measuring device, preferably a Sylvac P25 displacement probe 44, a linear variable differential transformer, or a similar type of device capable of measuring displacement accurately over a length of up to several inches. As illustrated, a displacement probe body 46 is mounted rigidly to the housing 24, so that a movable probe arm 48 contacts a sideways extension 50 of the rod 26. Relative movement of the rod 26 with respect to the housing 24 is detected by the relative movement of the arm 48 and the body 46. The probe 44 is provided with the required Sylvac electronic E25 analog board 52 and an Electrostatics 5 volt power supply 54 mounted within the housing 24.

It has been found in the presently preferred embodiment that the compression force applied to the specimen 40 through the transducers 36 and 38 should be controllable to differing levels to provide optimization of this parameter for different specimen materials and configurations. Once that optimal point has been reached, the force should be maintained precisely constant between different measurements of that specimen, and between different measurements that are to be compared with each other, in the tests to determine phase fractions, the preferred use of the present invention. For this purpose, a dead-loading system as described is fully operable and presently preferred.

However, it is desirable to fully automate the present apparatus 20, so that no operator is required, so that the testing may be controlled entirely by computer, and so that more complex loading patterns than dead loading may be used. It is believed that additional information may be achieved in testing using a force level that varies during the course of the test.

Figure 9:
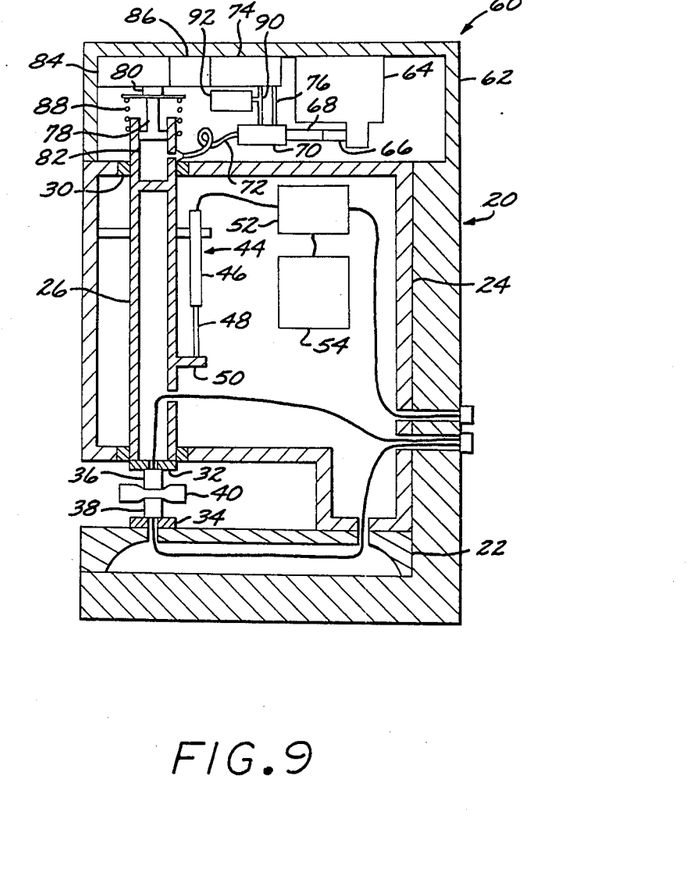
FIG. 9 is an alternative embodiment of apparatus for performing the loading.

To achieve this objective, an actively controlled force application device 60, illustrated in FIG. 9, is used in conjunction with the transducers 36 and 38. The device 60 includes a frame 62 surrounding the apparatus 20 illustrated in FIG. 1. The frame 62 includes a force application means supported in its upper head portion. A linear actuator 64 creates a rotational movement proportional to an input signal thereto. The rotational movement turns a collar 66 with an internal thread that moves a stationary screw 68, which in turn drives a hydraulic cylinder 70 to produce hydraulic pressure in a tube 72. The hydraulic cylinder 70 is filled from a reservoir 74 through a low pressure line 76.

A force piston 78 is supported from a force transducer 80 in the upper head of the frame 62. The upper end of the sliding rod 26 is modified to form a cylinder portion 82 which contains the piston 78. Hydraulic fluid from the tube 72 flows into the space between the piston 78 and the cylinder portion 82, causing a downward movement in the cylinder portion 82 and the rod 26, and thence in the transducer 36. When the transducer 36 contacts the specimen 40, a force is created which is measured in the force transducer 80. The signal from the force transducer 80 is sensed in a controller 84. This signal is compared to a command signal input by the person running the test, an automatic controller, or, preferably, a computer 86, and the difference used to control the linear actuator 64. Upon completion of the test, a return spring 88 aids in returning the cylinder portion 82 upwardly after hydraulic pressure has been released.

To assure that the pressure is applied to the specimen 40 in a uniform and smooth manner, a high pressure line 90 from the cylinder 70 communicates with an accumulator 92. The accumulator 92 is filled with pressurized gas, to cushion pressure rises in the high pressure line 90 and thence in the cylinder 70, the cylinder portion 82, and the transducer 36. The force is thereby applied to the specimen 40 in a smooth, uniform manner without impacts or force surges that could interfere with the measurements.

Returning to the dead-loading embodiment, which is presently preferred, FIG. 1 shows the specimen 40 with a constant weight applied. The transducers 36 and 38 act as punches to locally reduce the thickness of the specimen 40 in a central region 100 thereof, while the remainder of the specimen 40 retains its original thickness. The ultrasonic signals pass through the central region 100, and it is important to know the local through-thickness dimension in the central region 100. The thickness of a single ply of prepreg is typically about 0.005 inches, and a 0.001 inch reduction in thickness could result in a 20% error in the determination of ultrasonic velocity, if such error is undetected. The current local thickness is also required to determine the optimum time for taking the data.

The local dimension in the central region 100 is determined using the displacement probe 44 that measures the movement of the sliding rod 26. The housing 24 and rod 26 can be considered rigid, so that any movement of the rod 26 is due to the change in thickness of the specimen 40, after the transducer 36 is contacted to the top face of the specimen 40 and weight is applied. The local thickness of the specimen 40 is determined by placing the transducers 36 and 38 face to face without the specimen 40 present, and obtaining a displacement reading from the probe 44. The specimen 40 is then inserted between the transducers 36 and 38 with the transducers touching the opposing surfaces of the specimen 40 but without force being applied, and the displacement of the probe 44 is read again. The difference between the two readings is the local through thickness dimension of the specimen 40 in the central region 100, without applied force. The through thickness dimension of the specimen 40 with an applied force is determined by permitting the force of the rod 26 to be applied to the upper surface of the specimen 40 through the transducer 36, and continuously reading the displacement of the probe 44.

Figure 2:
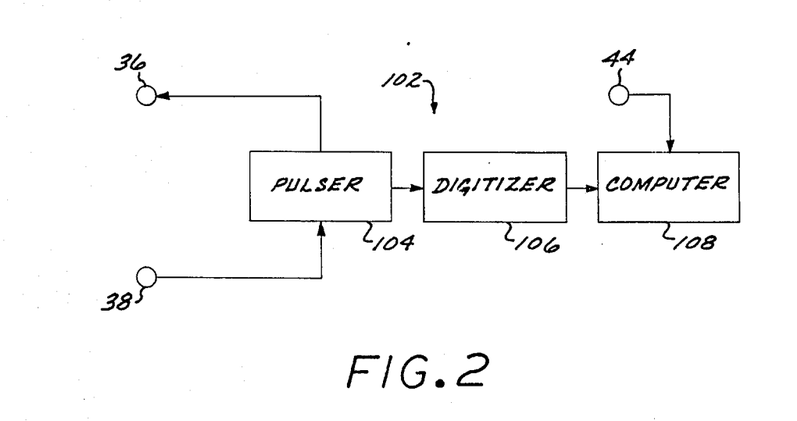
FIG. 2 is a functional block diagram of the control system of the apparatus of FIG. 1.

With the transducers 36 and 38 in place and compressively forced against the specimen 40, the ultrasonic measurements can be taken under the control of a controller 102, functionally illustrated in FIG. 2. The nature of these measurements depends upon the data required. In a preferred system, pulsed ultrasonic signals are emitted by transducer 36 under the control of a pulser 104. The pulser 104 sends a transmission pulse to the transducer 36, which transmits a corresponding signal into the specimen 40. The ultrasonic signal propagated through the specimen 40 and received by the transducer 38 is provided to the pulser 104. The waveform is digitized by a digitizer 106 and provided to a computer 108, which also receives the displacement signal from the displacement probe 44. The information in the computer 108 can then be used to calculate the desired properties such as velocity and attenuation as necessary, that in turn characterize the material. In the presently preferred embodiment, the pulser 104 is a General Research PCRR-100 programmable pulser, receiver, and the digitizer 106 is a Sonotek STR-825 programmable digitizer. The pulser 104 and digitizer 106 just described are available on cards, and can be inserted within the chassis of the computer 108, which is preferably an ALR 386/2 Model 40.

Ultrasonic measurements are taken using the apparatus 20 by raising the sliding rod 26 to separate the transducers 36 and 38, and inserting the specimen 40 into the gap between the transducers. For compliant specimens, no separate couplant is used. For other specimens, a drop of a completely volatile liquid couplant such as alcohol or water can be placed on the surface of each side of the specimen 40 in the region where the transducers 36 and 38 contact the specimen. The sliding rod 26 is lowered to permit the upper transducer 36 to rest against the specimen 40, and the measurements are taken. The sliding rod 26 is raised, and the process may be repeated with another area of the specimen 40 or another specimen. It will be appreciated that this apparatus 20 is well suited to an automated measurement operation, wherein a mechanism is provided to raise and lower the sliding rod 26 at the appropriate times, the force application device of FIG. 9 is used with an automatic controller, and another mechanism translates specimens into position between the transducers.

Figure 3:
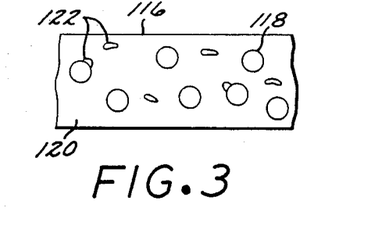
FIG. 3 is a schematic sectional view of a composite prepreg material having voids therein.

A typical piece of composite prepreg 116 is illustrated in FIG. 3, in a cross sectional view. The prepreg 116 is composed of a plurality of reinforcement fibers 118 embedded in a matrix 120. The view of FIG. 3 is in cross section to the fibers 118, so that they appear to be round in shape. In reality, the fibers 118 are elongated in the direction out of the plane of the drawing. Also found within the prepreg are compressible inclusions, specifically voids 122, such as air bubbles in the matrix 120 or at the interfaces between the fibers 118 and the matrix 120. (Other types of compressible inclusions, such as highly compliant third phases, are also possible, but generally only voids are found within the prepreg material of interest. Other types of compliant inclusions are treated in a manner similar to that of the voids as next discussed.) The air bubbles are normally present in the viscous liquid resin as a result of its mode of preparation, and also at the interfaces as a result of the manufacturing procedures. The voids 122 are removed during the high pressure curing of the laid up composite structure at a later time. However, the voids 122 are present in the prepreg 116 and cause errors to be made if phase fractions are determined without taking the voids into account.

Figure 4:
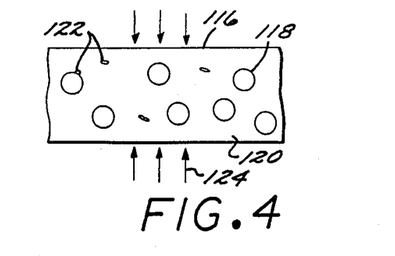
FIG. 4 is a schematic sectional view of the composite of FIG. 3, with the material slightly compressed to partially remove the voids.

FIG. 4 shows the prepreg 116 as it is being compressed by a through-thickness force 124, produced by the apparatus 20 in the manner previously described. The force 124 causes the voids 122 to be reduced in size and eventually eliminated. FIG. 4 illustrates the prepreg 116 at a time when a portion of the voids 122 are completely closed and therefore eliminated, and the remaining voids are reduced in size and will shortly be closed and eliminated.

Figure 5:
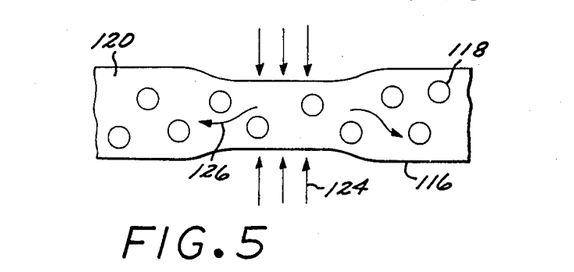
FIG. 5 is a schematic sectional view of the composite of FIG. 3, with the material further compressed to begin flow of matrix.

The force 124 also causes the flowable resin matrix 120 to deform and to flow out of the region affected by the compressive force, as indicated by the flow arrows 126 in FIG. 5. Just as the presence of voids 122 causes the measurement of phase fraction to be erroneous, as discussed in conjunction with FIG. 3, the flow of resin out of the compressed region also causes the measurement to be erroneous because the fraction of fibers as then determined is too high. The force 124 need not be gradually increased to create the progression illustrated in FIGS. 3-5. Continuous application of a constant force has the same effect.

The void collapse and matrix flow deformation mechanisms both contribute to, and account for, the deformation and thickness decrease of the specimen 40 in the central region 100, during the first several percent of deformation. However, the two mechanisms operate at different rates. The majority of the displacement measured by the probe 44 is attributable to the void collapse mechanism initially, but at higher displacements the voids 122 become nearly fully closed so that the void collapse mechanism is exhausted and contributes little to the further displacement. At the higher displacements, the resin flow mechanism accounts for virtually all of the displacement. The void collapse mechanism is thus said to be dominant at low displacements, and the resin flow mechanism is said to be dominant at high displacements. The point at which the contribution of the void collapse mechanism, termed the point of optimal consolidation, becomes less than the contribution of the matrix flow mechanism has important physical significance. At this optimal consolidation point the voids have disappeared, and the properties of the composite prepreg can be measured without their interference.

Figure 6:
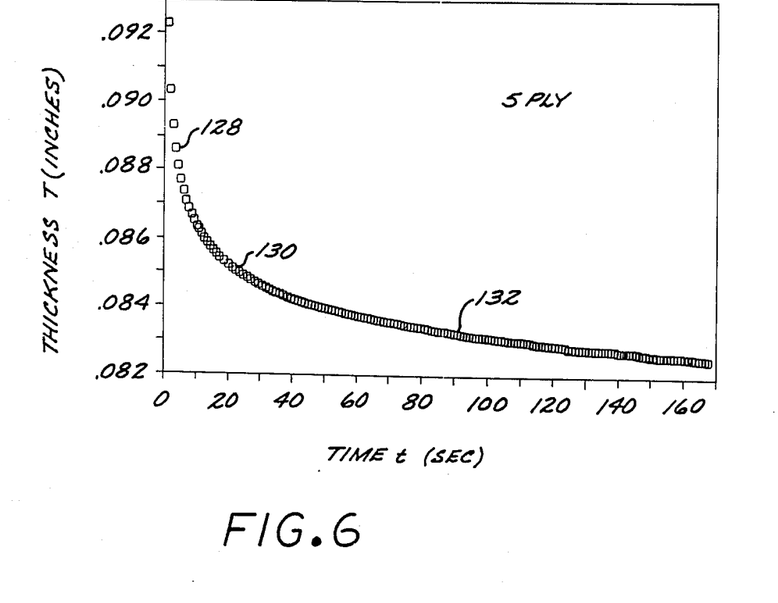
FIG. 6 is a graph of the change of measured thickness of the specimen under the compressive load with time.

FIG. 6 illustrates the thickness of the prepreg specimen 116 as a function of time, under a constant applied load, as measured by the probe 44 in actual test results recorded as squares. The thickness of the specimen 40 is reduced relatively rapidly during a first portion 128, goes through a transition region or knee 130, and then continues to fall, but more slowly, during a second portion 132. The rapid displacement change during the first portion 128 is due to the dominance of the void collapse mechanism, the displacement change during the second portion 132 is due to the operation of the resin flow mechanism, and the knee 130 is associated with the optimal consolidation point where the voids 122 have just been closed.

In the preferred approach, ultrasonic signals are continuously transmitted through the sample 40 by the transducers 36 and 38 during the first portion 128 and the knee 130, and into the early portion of the second portion 132. The time of flight of the ultrasonic pulse and the local thickness of the region 100 of the specimen 40 are recorded in the computer for later analysis. It is recognized that the data values taken during the first portion 128 are erroneous due to the presence of voids and that the data values taken during the second portion 132 are erroneous due to the extrusion of resin out of the region of compression. The data is stored so that the one correct value, taken at the knee 130, may be picked from the data and designated as the correct value.

Figure 7:
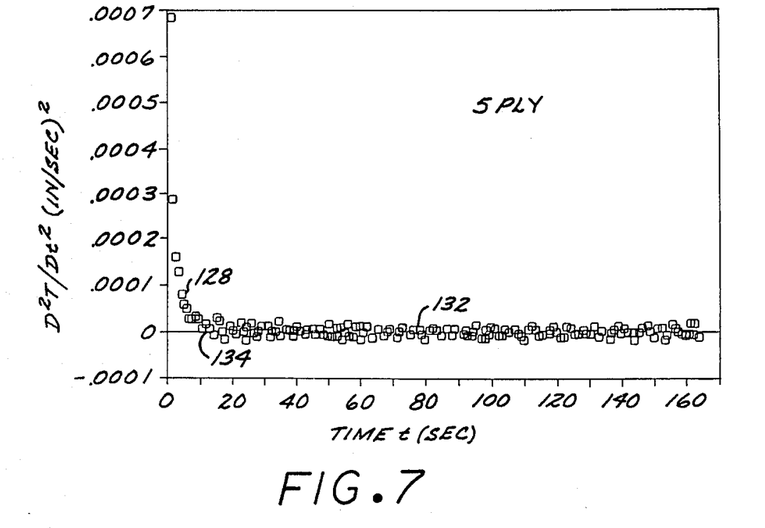
FIG. 7 is a graph of the second derivative of displacement with time, derived from the data of FIG. 6.

The knee 130 can be located in real time by utilizing well known computer programs to calculate the second derivative of the thickness T as a function of time, as illustrated in FIG. 7 for data taken from the curve of FIG. 6. The point at which the second derivative first becomes about zero, the point 134, corresponds to the closing of the voids and the replacement of void closing with resin extrusion as the dominant mechanism of deformation. At this point 134, the value of the average transit time, previously stored in the computer, may be designated as the standard material value. The local transit time divided by the local thickness, measured by the probe 44 at the time of the occurrence of the point 134 and the knee 130, is the composite "slowness". The transit time divided by the thickness at other times is also a measure of slowness, but is inaccurate for the reasons previously stated.

Figure 8:
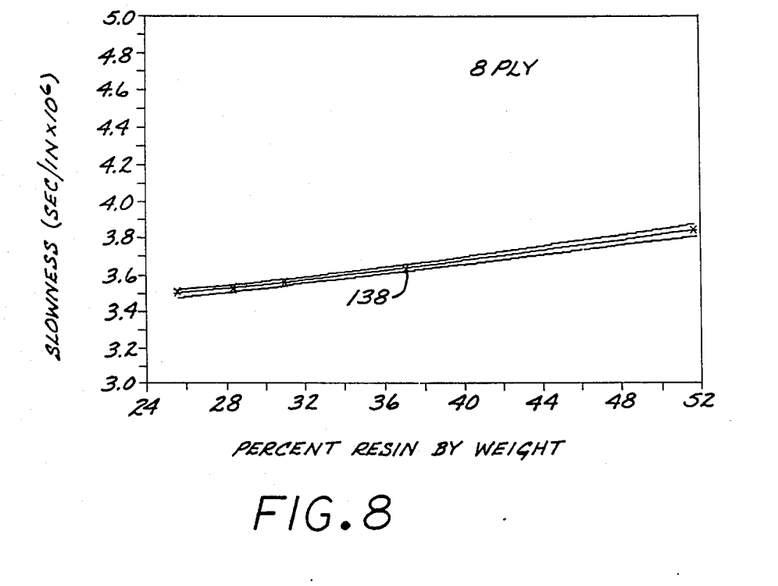
FIG. 8 is a graph of composite slowness as a function of phase fraction of resin matrix.

The composite slowness, defined as transit time divided by local thickness, measured at the optimal consolidation point, can be correlated directly and linearly with the phase fraction of the resin matrix, see FIG. 8, to enable phase fraction measurements of production or other specimens. Prepreg values obtained at other points than the optimal consolidation point do not exhibit the same types of correlations. Use of the optimal consolidation measurement technique thus provides significant advantages that cannot be obtained otherwise, in the defining and correlating of measurements.

A two-step process is followed. First, a basic correlation of slowness and phase fraction is established by calibration. Then, values of slowness for "unknown" specimens are plotted on the same graph on the correlation line, and the corresponding values of phase fraction are read from the graph.

The basic relation is established by measuring composite slowness in calibration specimens made of the same fiber and resin matrix materials as the subsequent specimens to be measured, and having phase fractions that are determined destructively. The results are plotted as the points 138 in FIG. 8. (The specimens were composite prepreg having carbon fibers in a curable epoxy matrix. Specifically, the specimens were Fiberite 934/T300 prepreg having unidirectional fibers. A stack of 5 plies was used with the sing around technique employed to measure the transit time.) In the usual practice, many more points 138 will be determined, and a least squares line fitted through the points. The fitted line becomes the correlation line for the subsequently tested "unknown" specimens. FIG. 8 demonstrates the high degree of correlation obtained and the linear fit.

It will normally be known that the production specimens to be tested as "unknowns" will be generally within a particular phase fraction range, as for example from 30 to 40 percent resin matrix. The calibration specimens used to derive the points 138 are then selected to have a range of phase fractions including the 30 to 40 percent range, and preferably outside the range so as to establish the fitted line with increasing confidence. In the graph of FIG. 8, the curved lines that bracket the data points are 95% confidence limits on the points 138, indicating that the error limit in determining the phase fractions is well under 1 percent. This limit of the confidence range is narrower than that experienced with conventional destructive procedures for obtaining phase fractions, and is attained far faster and at less cost.

The "unknown" specimens are typically production specimens of prepreg material for which measurements of composite slowness are made on the production line. The specimens are not destroyed, and the testing usually takes less than one minute, particularly where the testing operation is automated in the manner previously discussed.

The technique selected to measure the sample properties depends upon the thickness of the sample being measured. When the transit time is measured directly as the time between transmission and receipt of the ultrasonic wave through the specimen, the error limits of FIG. 8 typically increase as the number of plies of prepreg decreases, as a result of uncertainty in the measured transit time for the ultrasonic wave through the specimen. The minimum number of plies depends upon the material. As an example, for less than about 8 plies of thickness of the Fiberite 934/T300 material, the confidence limits exceed 1 percent, and are judged to be unacceptably broad. A stack of plies can be readily prepared by stacking several sheets for the purpose of the measurement.

Alternatively, a frequency measuring method may be used to determine the transit time of the specimen. In the preferred approach for measuring the transit time of the ultrasonic wave, the "sing around" technique, each reflected ultrasonic wave pulse triggers the next pulse. A measurable pulse frequency is thus established, and the reciprocal of the pulse frequency is related to the transit time of the ultrasonic signal.

The sing around approach has been applied to prepreg specimens having 1-8 plies, with excellent results. However, the transit time for a single ply is only about 90-100 nanoseconds. It is therefore necessary that care is taken to account for systematic errors in making the measurement.

Figure 10:
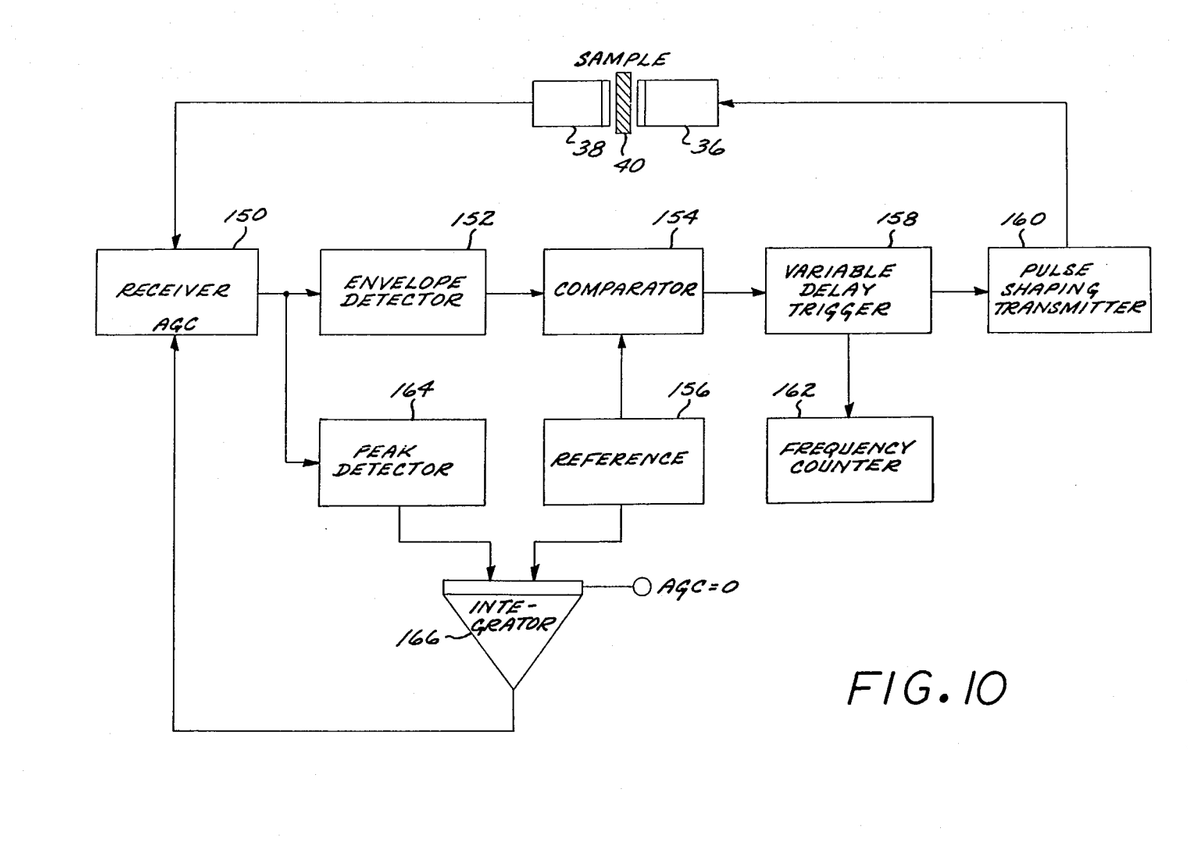
FIG. 10 is a functional block diagram for the apparatus and control circuit of a sing around measurement of composite ultrasonic properties.

A functional circuit outline for the sing around technique appears in FIG. 10. The specimen 40 is placed between and in contact with a transmitting transducer 36 and a receiving transducer 38, in the apparatus 20 described previously. An ultrasonic pulse transmitted by the transducer 36 is propagated through, delayed by, and modified by the receiving transducer 38. The transducer 38 transforms the mechanical sound energy into an electrical signal which is passed on to a receiver 150, where the signal is amplified. The envelope of the received signal is extracted by the envelope detector 152, and compared by a comparator 154 to a level provided by a reference 156. At a selected point on the envelope wave form a triggering signal is sent to a variable delay trigger 158 which, after a time delay causes a pulse shaper/transmitter 160 to generate another pulse and send it to the transmitting ultrasonic transducer 36.

Upon each repetition of the events described above, the variable delay trigger 158 sends a frequency signal to a frequency counter 162 whose output is recorded. The frequency measured by the counter 162 is inversely proportional to the time required for the occurrence of the events described in the preceding paragraph. To calibrate for systematic errors, the frequency is determined first with no specimen 40 in place and the transducers 36 and 38 in face-to-face contact. After the specimen 40 is put in place between the transducers 36 and 38, the additional delay corresponds to the transit time of the specimen material 40 and is reflected in a new value displayed by the counter 162.

For stability, the level of the signal provided by the receiver 150 must be independent of attenuation and coupling, and this state is achieved as follows. A peak detector 164 detects the maximum level of the received signal as provided by the receiver 150 and passes it to one summing input of an integrator 166. The negative of the desired peak level is provided by the reference circuit 156, and is applied to the other summing input of the integrator 166. The output of the integrator 166 is then returned to the automatic gain control input of the receiver 150 to insure that the peak level remains constant.

Thus, in the presently preferred approach, a frequency measuring technique is preferred for prepreg specimens having 1-7 plies, and a pulse-receiver method of direct transit time measurement is preferred for prepreg specimens having more than 7 plies.

The use of the optimal consolidation point has been described in conjunction with the determination of phase fractions, the presently preferred application. However, the recognition and determination of the optimal consolidation point is also significant as the composite displacement whereat voids or other compressible inclusions effectively disappear. This value is a standard reference for the beginning of void-free consolidation and curing of the prepreg material.

Although a particular embodiment of the invention has been described in detail for purposes of illustration, various modifications may be made without departing from the spirit and scope of the invention. Accordingly, the invention is not to be limited except as by the appended claims.

What is claimed is:

1. A process for measuring a standard reference deformation for a composite material, comprising the steps of:
    furnishing a specimen of a multiphase material wherein at least one phase is flowable, and which initially contains compressible inclusions within the specimen;
    compressing the specimen; and
    determining the deformation at which the dominant compressive displacement behavior of the composite material changes from that characteristic of collapse of the compressible inclusions to that characteristic of flow of the flowable phase, this deformation being the standard reference deformation.

2. The process of claim 1, including the further step of collecting data at the standard reference deformation.

3. The process of claim 1, wherein said compressible inclusions are voids.

4. A process for measuring a standard property of the phases of a multiphase material, comprising the steps of:
    furnishing a specimen of a multiphase material wherein at least one phase is flowable, and which initially contains compressible inclusions within the specimen;
    applying a compressive force to the specimen so that its deformation increases with increasing time; and
    measuring a property of the specimen at a standard specimen deformation at which the dominant compressive displacement behavior of the material changes from that characteristic of compressible inclusion collapse to that characteristic of flow of the flowable phase, the property measured at this point being the standard value of the property for the multiphase material.

5. The process of claim 4, wherein the standard specimen deformation is the deformation at which the second derivative of compressive displacement with time first falls to about zero.

6. The process of claim 4, wherein said steps of applying and measuring are performed by a single measurement means for measuring the property, which is forced against the surface of the specimen.

7. The process of claim 4, wherein said step of measuring is accomplished by
    performing a series of simultaneous measurements of the material displacement and the property being measured, and
    selecting from the series of data the property measured at the point whereat the dominant compressive behavior of the specimen changes from that characteristic of compressible inclusion collapse to that characteristic of flow of the flowable phase.

8. The process of claim 4, wherein the compressible inclusions are voids.

9. The process of claim 4, wherein the multiphase material is a composite prepreg.

10. The process of claim 4, wherein a property measured in said step of measuring is the time required for an ultrasonic wave to traverse the specimen.

11. A process for determining a standard property of a composite material, comprising the steps of:
    furnishing a specimen of a multiphase material wherein at least one phase is flowable, and which initially contains compressible inclusions within the specimen;
    contacting at least one surface of the specimen with an ultrasonic transducer under a compressive pressure so as to compress the composite material; and
    measuring the ultrasonic property of the specimen at the deformation at which the dominant compressive displacement behavior of the composite material changes from that characteristic of compressible inclusion collapse to that characteristic of flow of the flowable phase, the property measured at this point being the standard value of the property for the composite material.

12. The process of claim 11, wherein the property measured is the ultrasonic slowness.

13. The process of claim 11, wherein the property is measured by the transit time technique.

14. The process of claim 11, wherein the property is measured by the sing around technique.

15. The process of claim 11, wherein the pressure applied varies during said step of measuring.

16. The process of claim 11, including the further step of:

comparing the standard value of the property for the specimen with standard values determined for other specimens whose phase fractions are known, to ascertain the phase fraction of the specimen.

17. A process for measuring the fractions of the phases of a composite material, comprising:

furnishing a specimen of a composite material having a reinforcement phase embedded within a flowable matrix phase, and further having voids therein;

contacting at least one surface of the specimen with an ultrasonic transducer under a downward compressive pressure;

determining the displacement of the transducer with time;

measuring the velocity of ultrasonic wave propagation of the specimen as the dominant compressive displacement behavior of the specimen changes from that characteristic of void collapse to that characteristic of flow of the flowable phase; and calculating the fractions of the phases present in the composite material from the velocity of ultrasonic wave propagation measured in said step of measuring.

18. The process of claim 17, wherein the specimen deformation is measured as the deformation at which the second derivative of compressive displacement with time falls to about zero.

* * * * *